(12) United States Patent
Inoue et al.

(10) Patent No.: US 7,993,929 B2
(45) Date of Patent: Aug. 9, 2011

(54) METHOD FOR DETERMINATION OF PRESENCE OR ABSENCE OF PEPTIDE COMPOUND PYY$_{3-36}$

(75) Inventors: Yoshihisa Inoue, Osaka (JP); Mikhail Rekharsky, Hyogo (JP); Kimoon Kim, Pohang (KR); Yong Ho Ko, Pohang (KR); Narayanan Selvapalam, Pohang (KR)

(73) Assignee: Japan Science and Technology Agency, Saitama (JP)

( * ) Notice: Subject to any disclaimer, the term of this patent is extended or adjusted under 35 U.S.C. 154(b) by 165 days.

(21) Appl. No.: 12/463,889

(22) Filed: May 11, 2009

(65) Prior Publication Data

US 2010/0009453 A1 Jan. 14, 2010

Related U.S. Application Data (63) Continuation of application No. PCT/JP2007/070785, filed on Oct. 25, 2007.

(30) Foreign Application Priority Data

Nov. 9, 2006 (JP) .................................. 2006-304529

(51) Int. Cl.
   *G01N 25/20* (2006.01)
(52) U.S. Cl. .......................... 436/86; 436/147; 436/815
(58) Field of Classification Search .................... 436/86, 436/147, 815
See application file for complete search history.

(56) References Cited

U.S. PATENT DOCUMENTS

2004/0265237 A1 12/2004 Kim et al.
2005/0080068 A1 4/2005 Isaacs et al.

FOREIGN PATENT DOCUMENTS

JP 2005-503415 A 2/2005
WO 03/024978 3/2003

OTHER PUBLICATIONS

M. Rekharsky et al., "Chiral Recognition in Cucurbituril Cavities," Journal of the American Chemical Society, 2006, vol. 128, p. 14871-14880.
Pearlman et al., "Pharmaceutics of Protein Drugs," J. Pharm. Pharmacol., 1992, 44, p. 178-185.
Strickley et al., "An Unexpected pH Effect on the Stability of Moexipril Lyophilized Powder," Pharm. Res., 1989, 6, p. 971-975.
Bhatt et al., "Chemical Pathways of Peptide Degradation. I. Deamidation of Adrenocorticotropic Hormone," Pharm. Res., 1990, 7, p. 593-599.
Jordan et al., "The Aggreation of Bovine Serum Albumin in Solution and in the Solid State," J. Pharm. Pharmacol., 1994, 46, p. 182-185.
Lai et al., "Solid-State Chemical Stability of Proteins and Peptides," J. Pharm. Sci., 1999, 88, p. 489-500.

(Continued)

*Primary Examiner* — Jill Warden
*Assistant Examiner* — Monique Cole
(74) *Attorney, Agent, or Firm* — Greenblum & Bernstein, PLC (57) ABSTRACT

The present invention provides a method for determining in a pharmaceutical test formulation the presence or absence of a peptide compound PYY$_{3-36}$ represented by the following amino acid sequence: H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-X (SEQ ID NO: 1), wherein X is OH or a carboxy acid-protecting group, the method comprising (1) preparing a solution by mixing the pharmaceutical test formulation with cucurbit[7]uril in a solvent; and (2) thermally analyzing the solution prepared in Step (1).

3 Claims, 3 Drawing Sheets

OTHER PUBLICATIONS

Kertscher et al., "Spontaneous Chemical Degradation of Substance P in the Solid Phase and in Solution," Int. J. Pept. Protein Res., 1993, 41, p. 207-211.

U.S. Appl. No. 12/514,280 entitled "Method for Determination of Presence or Absence of Peptide Compound $PYY_{3-36}$," to Inoue et al., which application is the National Stage of PCT/JP2007/070785, filed Oct. 25, 2007.

U.S. Appl. No. 12/446,718 entitled "Method for Determining Quantity of Peptide Compound Having Phenylalanine Residue at N-Terminus," to Inoue et al., which application is the National Stage of PCT/JP2007/070656, filed Oct. 23, 2007.

METHOD FOR DETERMINATION OF PRESENCE OR ABSENCE OF PEPTIDE COMPOUND PYY$_{3-36}$

CROSS-REFERENCE TO RELATED APPLICATIONS

The present application is a Continuation of International Patent Application No. PCT/JP2007/070785, filed on Oct. 25, 2007, and claims priority under 35 U.S.C. §119 of Japanese Patent Application No. 2006-304529, filed Nov. 9, 2006, the contents of which are expressly incorporated by reference herein in their entireties.

TECHNICAL FIELD

The present invention relates to a method for determining the presence or absence of peptide compound PYY$_{3-36}$.

BACKGROUND ART

Recently, the harmful effects of obesity on health have become a problem. Long-term or invasive treatment is required to promote and sustain weight loss. According to the U.S. Department of Health and Human Services, approximately 300,000 deaths a year in the United States are associated with obesity, and the direct and indirect costs attributed to obesity exceed $100 billion.

Heretofore, anorectic agents such as sibutramine, phentermine, and orlistat have been commercially available; however, they have unsatisfactory appetite-suppressing effects.

There has been growing expectation in recent years that natural peptide hormone, effective for regulating appetite, will be used in medical applications. Several pharmaceutical companies have started clinical trials and preclinical trials regarding the role of natural peptide hormone in obesity.

In particular, a peptide compound PYY$_{3-36}$ (hereinafter, sometimes abbreviated as "PYY$_{3-36}$") represented by the following amino acid sequence: H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-X (SEQ ID NO: 1), wherein X is OH or a carboxy acid-protecting group, has been receiving attention as a natural peptide hormone. Intranasal administration of PYY$_{3-36}$ has already been offered as a novel obesity treatment method. PYY$_{3-36}$ is included in secretions (hereinafter, sometimes referred to as a "secretion") produced by endocrine cells of the human gut, particularly the stomach. The secretion is readily released based on human food intake, etc.

The secretion usually includes a peptide compound PYY$_{1-36}$ (hereinafter, sometimes abbreviated as "PYY$_{1-36}$") represented by the following amino acid sequence: H-Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-NH$_2$ (SEQ ID NO: 2). PYY$_{1-36}$ is a compound in which "Tyr-Pro-" is further bound to the N-terminal of PYY$_{3-36}$, and has a similar amino acid sequence to PYY$_{3-36}$.

When trypsin is present in the secretion, the trypsin may cleave PYY$_{1-36}$ and PYY$_{3-36}$, which generates new peptide digests.

Pharmaceutical formulations containing PYY$_{3-36}$ can be made, for example, by extracting PYY$_{3-36}$ from the secretion. However, PYY$_{1-36}$, and peptide digests derived from PYY$_{1-36}$ or PYY$_{3-36}$ may also be present in the pharmaceutical formulations during production.

When the pharmaceutical formulation containing PYY$_{3-36}$ is in solid form (tablets, powders, etc.), PYY$_{3-36}$ may be degraded due to long-term storage, which results in the presence of peptide digests derived from PYY$_{3-36}$ in the pharmaceutical formulation. It has been known that a solid peptide compound can be less stable than a compound in a solution (Non-patent Documents 1 to 4). In a solid peptide compound, a peptide bond is easily cleaved (Non-patent Document 5). Especially, when a peptide compound includes an arginine residue therein, the bond between the arginine residue and the amino acid residue adjacent thereto is easily breakable (Non-patent Document 6).

Therefore, in the PYY$_{3-36}$-containing pharmaceutical formulation, it is important to determine the presence or absence of PYY$_{3-36}$, i.e., the presence or absence of peptide digests derived from PYY$_{3-36}$ during production or after long-term storage. Additionally, when a pharmaceutical formulation is made by extracting PYY$_{3-36}$ from a secretion, it is preferable to determine the presence or absence of PYY$_{1-36}$ and peptide digests derived from PYY$_{1-36}$ during production.

Examples of the determination method include an HPLC method and electrophoresis.

However, PYY$_{3-36}$, PYY$_{1-36}$, and the peptide digests thereof have a common amino acid sequence from the C-terminal; therefore, it is difficult to determine the presence or absence of PYY$_{3-36}$ using known methods. Further, the determination of the complete amino acid sequences of all peptide compounds contained in a pharmaceutical formulation is both time consuming and complicated.

Non-Patent Document 1:
Pearlman, R.; Nguyan, T. J., J. Pharm. Pharmacol. 1992, 44, 178
Non-Patent Document 2:
Strickley, R. G.; Visor, G. C.; Lin, L.; Gu, L., Pharm. Res. 1989, 6, 971
Non-Patent Document 3:
Bhatt, N.; Patel, K.; Borchart, R. T., Pharm. Res. 1990, 7, 593
Non-Patent Document 4:
Jordan, G. M.; Yoshioka, S.; Terao, T., J. Pharm. Pharmacol. 1994, 46, 182
Non-Patent Document 5:
Lai, M. C.; Topp, E. M., J. Pharm. Sci. 1999, 88, 489
Non-Patent Document 6:
Kertscher, U.; Bienert, M.; Krause, E.; Sepetov, N. F.; Mehlis, B., Int. J. Pept. Protein Res. 1993, 41, 207

DISCLOSURE OF THE INVENTION

Problems to be Solved by the Invention

The main object of the present invention is to provide a method for easily and accurately determining the presence or absence in a pharmaceutical formulation of a peptide compound PYY$_{3-36}$ represented by the following amino acid sequence: H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-X (SEQ ID NO: 1), wherein X is OH, or carboxy acid-protecting group.

Means for Solving the Problems

In view of the problems of the foregoing prior art, the present inventors conducted extensive research. As a result, they found that a specific determination method can achieve the aforementioned object. The present invention has been accomplished based on this finding.

The present invention relates to the following determination method.

Item 1

A method for determining in a pharmaceutical test formulation the presence or absence of a peptide compound $PYY_{3-36}$ represented by the following amino acid sequence: H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-X (SEQ ID NO: 1), wherein X is OH or a carboxy acid-protecting group, the method comprising:

(1) preparing a solution by mixing the pharmaceutical test formulation with cucurbit[7]uril in a solvent; and
(2) thermally analyzing the solution prepared in Step (1).

Item 2

The determination method according to Item 1, wherein the presence or absence of a peptide compound $PYY_{1-36}$ represented by the following amino acid sequence: H-Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-$NH_2$ (SEQ ID NO: 2), and/or peptide digests generated by degradation of the peptide compound $PYY_{1-36}$ is determined.

Item 3

The determination method according to Item 1, wherein peptide digests generated by degradation of the peptide compound $PYY_{3-36}$ is detected.

The present invention relates to a method for determining in a pharmaceutical formulation to be tested the presence or absence of a peptide compound $PYY_{3-36}$ represented by the following amino acid sequence: H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-X (SEQ ID NO: 1), wherein X is OH or a carboxy acid-protecting group, which comprises the steps of (1) preparing a solution by mixing the pharmaceutical test formulation with a cucurbit[7]uril in a solvent; and (2) thermally analyzing the solution prepared in Step (1).

Examples of the carboxy acid-protecting group include $NH_2$, NH—$R^1$, $NHCOR^2$, $OR^3$, SH, $SR^4$, etc.

Examples of $R^1$ include an optionally substituted saturated hydrocarbon group, an optionally substituted aryl group, an optionally substituted heteroaryl group, an optionally substituted aralkyl group, etc.

Optionally substituted saturated hydrocarbon groups are not particularly limited. Specific examples thereof include $C_{1-20}$ linear or branched alkyl groups and $C_{3-12}$ cycloalkyl groups. Specific examples of $C_{1-20}$ linear or branched alkyl groups include methyl, ethyl, propyl, isopropyl, butyl, isobutyl, sec-butyl, tert-butyl, pentyl, hexyl, heptyl, octyl, nonyl, decyl, undecyl, dodecyl, icosyl, etc. Specific examples of $C_{3-12}$ cycloalkyl groups include cyclopropyl, cyclobutyl, cyclopentyl, cyclohexyl, cycloheptyl, cyclododecyl, etc.

Substitute groups of optionally substituted saturated hydrocarbon groups are not particularly limited. Specific examples thereof include alkoxy, aryloxy, siloxy, dialkylamino, etc. Examples of alkoxy groups include $C_{1-6}$ alkoxy groups. Specific examples include methoxy, ethoxy, hexyloxy, etc. Examples of aryloxy groups include $C_{6-12}$ aryloxy groups, such as phenoxy, naphthyloxy, etc. Examples of siloxy groups include trimethylsiloxy, triethylsiloxy, triisopropylsiloxy, tert-butyldimethylsiloxy, etc. Examples of dialkylamino groups include dimethylamino, diethylamino, etc.

The substitution site and the number of substituents of optionally substituted saturated hydrocarbon groups are not particularly limited sofar as the effect of the invention is not impaired.

Optionally substituted aryl groups are not particularly limited, and include $C_{6-14}$ aryl. Specific examples thereof include phenyl, 1-naphthyl, 2-naphthyl, biphenylyl, anthryl, etc.

Substitute groups of optionally substituted aryl groups are not limited sofar as the effect of the invention is not impaired. Specific examples thereof include $C_{1-6}$ alkyl, $C_{6-14}$ aryl, 5 to 10-membered aromatic heterocycle, alkoxy, aryloxy, siloxy, dialkylamino, etc.

Examples of $C_{1-6}$ alkyl groups include methyl, ethyl, propyl, isopropyl, butyl, isobutyl, sec-butyl, tert-butyl, pentyl, hexyl, etc.

Examples of $C_{6-14}$ aryl groups include phenyl, 1-naphthyl, 2-naphthyl, biphenylyl, 2-anthryl, etc.

Examples of 5 to 10-membered aromatic heterocycles include 2-, or 3-thienyl; 2-, 3-, or 4-pyridyl; 2-, 3-, 4-, 5-, or 8-quinolyl; 1-, 3-, 4-, or 5-isoquinolyl; 1-, 2-, or 3-indolyl; 2-benzothiazolyl; 2-benzo[b]thienyl; benzo[b]furanyl; etc.

Examples of alkoxy groups include $C_{1-6}$ alkoxy groups, such as methoxy, ethoxy, hexyloxy, etc.

Examples of aryloxy groups include $C_{6-12}$ aryloxy groups, such as phenoxy, naphthyloxy, etc.

Examples of siloxy groups include trimethylsiloxy, triethylsiloxy, triisopropylsiloxy, tert-butyldimethylsiloxy, etc.

Examples of dialkylamino groups include dimethylamino, diethylamino, etc.

The substitution site and the number of substituents of optionally substituted aryl groups are not particularly limited sofar as the effect of the invention is not impaired.

Optionally substituted heteroaryl groups are not particularly limited. Examples thereof include optionally condensed 5 to 14-membered aromatic heterocycles with 1 to 3 atoms selected from sulfur atoms, oxygen atoms, and nitrogen atoms. Specific examples include furil, thienyl, pyrrolyl, pyrazolyl, imidazolyl, oxazolyl, isoxazolyl, isothiazolyl, thiazolyl, 1,2,3-oxadiazolyl, triazolyl, tetrazolyl, thiadiazolyl, pyridyl, pyridazinyl, pyrimidinyl, pyrazinyl, indolyl, indazolyl, purinyl, quinolyl, isoquinolyl, phthalazinyl, naphthyridinyl, quinoxalinyl, quinazolinyl, cynolinyl, pteridinyl, carbazolyl, carbonyl, phenanthridinyl, acridinyl, etc.

The type, substitution site, and number of substituents of optionally substituted heteroaryl groups are the same as those described in the description of the aryl groups.

Examples of optionally substituted aralkyl groups include benzyl, phenethyl, phenylpropyl, etc. The type, substitution site, and number of substituents of optionally substituted aralkyl groups are the same as those described in the description of the aryl group.

Examples of $R^2$, $R^3$, and $R^4$ are the same as those of $R^1$ above.

Methyl and ethyl groups are preferably used as $R^1$, $R^2$, $R^3$, and $R^4$. When $R^1$, $R^2$, $R^3$, and $R^4$ are methyl or ethyl groups, $PYY_{3-36}$ can be suitably dissolved in water, which is used as a solvent, during the production of the solution described later.

In particular, X is preferably $NH_2$ in the determination method of the present invention.

The present invention relates to a method for determining the presence or absence of $PYY_{3-36}$ in a pharmaceutical test formulation. $PYY_{3-36}$ can be extracted from a secretion produced by endocrine cells of the human gut, particularly the stomach. When the pharmaceutical test formulation is made using the obtained secretion, $PYY_{1-36}$ and digests thereof may also be present in the pharmaceutical formulation. When a pharmaceutical formulation containing $PYY_{3-36}$ is stored for a long period of time, $PYY_{3-36}$ may be degraded to generate peptide digests. Particularly, the bond between arginine and tyrosine inside $PYY_{1-36}$ and $PYY_{3-36}$ is relatively weaker than the bond between other amino acids, and is more easily broken. Accordingly, $PYY_{1-36}$ is degraded (the bond between arginine and tyrosine is broken), which allows for easy generation of peptide digests having a tyrosine residue at the N-terminal. Further, the degradation of $PYY_{3-36}$ (the bond between arginine and tyrosine is broken) allows for easy generation of peptide digests having a tyrosine residue at the N-terminal and peptide digests having an isoleucine residue at the N-terminal.

$PYY_{1-36}$, peptide digests derived from $PYY_{1-36}$, and peptide digests derived from $PYY_{3-36}$, each having a tyrosine residue at the N-terminal, are reacted (forming a complex) with cucurbit[7]uril (hereinafter, sometimes referred to as "CB[7]") to generate heat. According to the determination method of the present invention, the presence or absence of $PYY_{3-36}$ can be determined by detecting $PYY_{3-36}$-derived peptide digests having a tyrosine residue at the N-terminal through the thermal analysis of the mixture obtained by mixing the pharmaceutical test formulation and CB[7] in a solution. Further, the purity of $PYY_{3-36}$ in the pharmaceutical test formulation can be measured by detecting $PYY_{1-36}$ and $PYY_{1-36}$-derived peptide digests both having a tyrosine residue at the N-terminal.

Step (1)

In Step (1), the pharmaceutical test formulation is mixed with cucurbit[7]uril in a solvent to prepare a solution.

Pharmaceutical Test Formulation

According to the determination method of the invention, the presence or absence of $PYY_{3-36}$ in the pharmaceutical test formulation can be determined. That is, the presence or absence of $PYY_{3-36}$ (the presence or absence of $PYY_{3-36}$ degradation) can be determined by detecting peptide digests that are generated as a result of $PYY_{3-36}$ degradation.

Examples of peptide digests generated as a result of $PYY_{3-36}$ degradation include those having a tyrosine residue at the N-terminal, those having an isoleucine residue at the N-terminal, etc.

Examples of $PYY_{3-36}$-derived peptide digests having a tyrosine residue at the N-terminal (hereinafter sometimes abbreviated as "Digest A") include Tyr-X, Tyr-Leu-Asn-Leu-Val-Thr-Arg-Gln-Arg-Tyr-X (SEQ ID NO: 3), Tyr-Tyr-Ala-Ser-Leu-Arg-His-Tyr-Leu-Asn-Leu-Val-Thr-Arg-Gln-Arg-Tyr-X (SEQ ID NO: 4), Tyr-Tyr-Ala-Ser-Leu-Arg-His (SEQ ID NO: 5), Tyr-Tyr-Ala-Ser-Leu-Arg-His-Tyr-Leu-Asn-Leu-Val-Thr-Arg-Gln-Arg (SEQ ID NO: 6), Tyr-Leu-Asn-Leu-Val-Thr-Arg-Gln-Arg (SEQ ID NO: 7), etc. These may be used singly or in a combination of two or more in a pharmaceutical test formulation.

Examples of $PYY_{3-36}$-derived peptide digests having an isoleucine residue at the N-terminal (hereinafter sometimes abbreviated as "Digest B") include H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg (SEQ ID NO: 8), H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His (SEQ ID NO: 9), H-Ile-Lys-Pro-Glu-Ala-Pro-Gly-Glu-Asp-Ala-Ser-Pro-Glu-Glu-Leu-Asn-Arg (SEQ ID NO: 10). These may be used singly or in a combination of two or more in a pharmaceutical test formulation.

According to the determination method of the present invention, the presence or absence of peptide compound $PYY_{1-36}$ represented by the following amino acid sequence: H-Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-$NH_2$ (SEQ ID NO: 2), and/or peptide digests that are generated by the degradation of peptide compound $PYY_{1-36}$ can be determined in a pharmaceutical test formulation.

Examples of peptide digests generated by the degradation of $PYY_{1-36}$ include those having a tyrosine residue at the N-terminal.

Examples of $PYY_{1-36}$-derived peptide digests having a tyrosine residue at the N-terminal (hereinafter sometimes abbreviated as "Digest C") include Tyr-$NH_2$, Tyr-Leu-Asn-Leu-Val-Thr-Arg-Gln-Arg-Tyr-$NH_2$ (SEQ ID NO: 11), Tyr-Tyr-Ala-Ser-Leu-Arg-His-Tyr-Leu-Asn-Leu-Val-Thr-Arg-Gln-Arg-Tyr-$NH_2$ (SEQ ID NO: 12), Tyr-Tyr-Ala-Ser-Leu-Arg-His (SEQ ID NO: 5), Tyr-Tyr-Ala-Ser-Leu-Arg-His-Tyr-Leu-Asn-Leu-Val-Thr-Arg-Gln-Arg (SEQ ID NO: 6), Tyr-Leu-Asn-Leu-Val-Thr-Arg-Gln-Arg (SEQ ID NO: 7), H-Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg (SEQ ID NO: 13), H-Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His (SEQ ID NO: 14), H-Tyr-Pro-Ile-Lys-Pro-Glu-Ala-Pro-Gly-Glu-Asp-Ala-Ser-Pro-Glu-Glu-Leu-Asn-Arg (SEQ ID NO: 15), and the like. These may be used singly or in a combination of two or more in a pharmaceutical test formulation.

The amounts of $PYY_{3-36}$, Digest A, Digest B, $PYY_{1-36}$, and Digest C in a pharmaceutical test formulation are not particularly limited. According to the determination method of the invention, when at least one member selected from the group consisting of Digest A having a tyrosine residue at the N-terminal, $PYY_{1-36}$, and Digest C is contained in an amount 1 wt % or more in total, Digest A or the like can be suitably detected, which makes it possible to determine the presence or absence of $PYY_{3-36}$ with high accuracy.

The pharmaceutical test formulation may include the following known components, which are usually contained in pharmaceutical formulations. For example, peptide compounds other than $PYY_{3-36}$, Digest A, Digest B, $PYY_{1-36}$, and Digest C may be contained.

The forms of pharmaceutical formulations are not particularly limited. Typical examples include tablets, pills, powders, solutions, suspensions, emulsions, granules, capsules, suppositories, injections (solutions, suspensions, etc.) and the like. In the examination method of the invention, pharmaceutical formulations in such forms can be used singly or in a combination of two or more.

CB[7]

Figure 1:
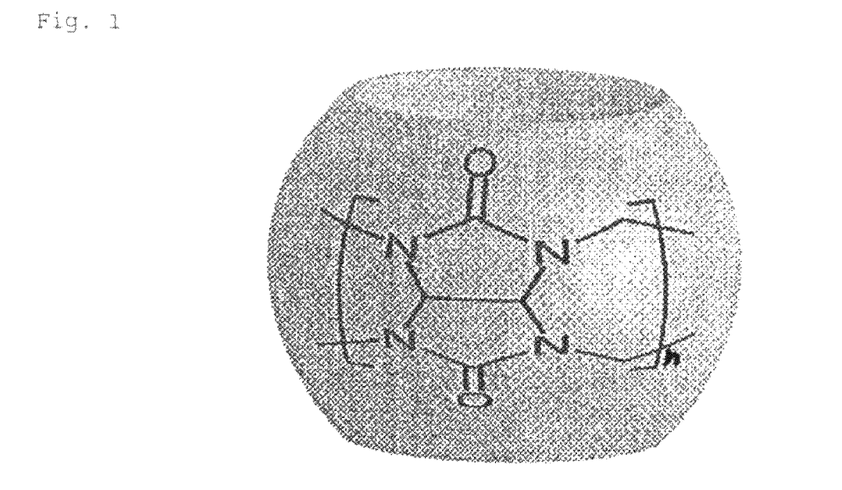
FIG. 1 shows a chemical structure of cucurbit[7]uril.

CB[7] is a barrel-shaped molecule, which is shown in FIG. 1.

The presence or absence of $PYY_{3-36}$ cannot be determined with high accuracy when cucurbiturils (e.g., cucurbit[6]uril, cucurbit[8]uril) other than cucurbit[7]uril are used.

Solution Preparation

The solution is prepared by mixing the pharmaceutical test formulation with CB[7] in a solvent.

When the pharmaceutical test formulation includes Digest A, $PYY_{1-36}$, Digest C, etc., mixing the pharmaceutical test formulation with CB[7] in a solution causes at least one peptide compound selected from Digest A, $PYY_{1-36}$, and Digest C to react with CB[7] (forming a complex); and generates heat.

Usable solvents are not particularly limited, but the solvent is preferably water. CB[7] can be suitably dissolved in water.

The concentration of the pharmaceutical test formulation in the solution is not particularly limited, but is preferably 0.01 to 1 mmol/l, more preferably 0.02 to 0.5 mmol/l, and most preferably 0.02 to 0.05 mmol/l.

The concentration of CB[7] in the solution is not particularly limited, but is preferably 0.1 to 10 mmol/l, more preferably 0.2 to 5 mmol/l, and most preferably 0.2 to 0.5 mmol/l.

The pH of the solution is not limited, but preferably 1 to 8, more preferably 3 to 8, and most preferably 5 to 7. In particular, the degradation of $PYY_{3-36}$, $PYY_{1-36}$ or the like can be further prevented at a pH of 3 or more.

In the determination method of the present invention, the solution may include salt, but preferably not. Salt often prevents a reaction (complex formation) of CB[7] with Digest A or the like.

Examples of salts include neutral salts that are dissolved in a solution of $Na_2SO_4$, $K_2SO_4$, $MgSO_4$, NaCl, KCl, $MgCl_2$, $NaNO_3$, $KNO_3$, $Mg(NO_3)_2$, $Ca(NO_3)_2$, $Na_3PO_4$, $K_3PO_4$, etc; slightly acidic salts that are dissolved in a solution of $NaH_2PO_4$, $KH_2PO_4$, etc; slightly basic salts that are dissolved in a solution of $Na_2CO_3$, $NaHCO_3$, $K_2CO_3$, $KHCO_3$, $Na_2HPO_4$, $K_2HPO_4$, $CH_3COONa$, and $CH_3COOK$, etc. Such salts can be used singly or in a combination of two or more.

The concentration of salt in a solution is generally 0.5 mol/l or less, preferably 0.1 mol/l or less, more preferably 10 mmol/l or less, and most preferably 0 to 1 mmol/l. When the concentration of salt in a solution is more than 0.5 mol/l, a reaction (complex formation) of CB[7] with Digest A or the like is difficult to proceed. When the concentration of salt in a solution is more than 10 mmol/l, a reaction (complex formation) between CB[7] and Digest A or the like suitably advances, which makes it possible to determine the presence or absence of $PYY_{3-36}$ with high accuracy.

The mixing method is not particularly limited. For example, the thermal analysis in Step (2) is conducted using an isothermal titration calorimeter in the following manner. The solution that is formed by the dissolution of CB[7] and salt in a solvent (hereinafter sometimes referred to as "Solution B") is added dropwise by a specified amount (e.g., 0.01 ml) to the solution formed by the dissolution of the pharmaceutical formulation in the solvent (hereinafter sometimes referred to as "Solution A") under thermal balance.

The concentration of the pharmaceutical test formulation in Solution A is not limited, but is preferably 0.01 to 1 mmol/l, more preferably 0.02 to 0.5 mmol/l, and most preferably 0.02 to 0.05 mmol/l. The concentration of CB[7] in Solution B is not limited, but is preferably 0.1 to 10 mmol/l, more preferably 0.2 to 5 mmol/l, and most preferably 0.2 to 0.5 mmol/l.

The concentration of salt in Solution B is not limited, but is preferably 10 mol/l or less, and more preferably 0 to 2 mmol/l.

Step (2) will be described in detail below with reference to examples in which the determination method of the invention is performed using an isothermal titration calorimeter.

Step (2)

In Step (2), the solution obtained in Step (1) is thermally-analyzed. Specifically, the amount of heat is quantified each time Solution B is added dropwise. The known calorimeters may be used for thermal analysis of the solution. In the present invention, it is particularly preferable to use an isothermal titration calorimeter for measurement of heat.

In the determination method of the invention, heat generated during the mixing of pure $PYY_{3-36}$ and CB[7] in a solution is quantified before solution preparation in Step (1). Namely, a calibration curve is prepared in advance.

A $PYY_{3-36}$-containing solution and Solution B are first prepared, and Solution B may be added dropwise to the $PYY_{3-36}$-containing solution by a certain amount (e.g., 0.01 ml per each).

The $PYY_{3-36}$-containing solution can be prepared by dissolving $PYY_{3-36}$ in the above-mentioned solvent.

The concentration of $PYY_{3-36}$ in the $PYY_{3-36}$-containing solution is not limited as long as the concentration is approximately equivalent to that of Solution A, and preferably 0.01 to 1 mmol/l, more preferably 0.02 to 0.5 mmol/l, and most preferably 0.02 to 0.05 mmol/l.

The calibration curve can be prepared by plotting the molar ratio of $PYY_{3-36}$ and the added CB[7] on the abscissa and the amount of heat generated at each drop on the ordinate.

The presence or absence of $PYY_{3-36}$ in the pharmaceutical test formulation can be determined by comparing the plot of the amounts of heat on the calibration curve and that obtained through the heat analysis of the solution prepared in Step (1). Specifically, it is possible to determine the presence or absence of $PYY_{1-36}$, Digest C, or the like during production; and it is possible to determine if $PYY_{3-36}$ is not degraded but effectively present in the long-stored pharmaceutical formulation.

Effects of the Invention

According to the determination method of the invention, the presence or absence of peptide compound $PYY_{3-36}$ represented by the following amino acid sequence: H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-X (SEQ ID NO: 1), wherein X is OH, or a carboxy acid-protecting group that can be easily and accurately (range of error within approximately 1 to 2%) determined in a pharmaceutical formulation. Specifically, according to the determination method of the invention, the presence or absence of $PYY_{3-36}$ in a long-stored pharmaceutical formulation can be determined by detecting peptide digests generated by peptide compound $PYY_{3-36}$ degradation. Further, according to the determination method of the invention, the presence or absence of $PYY_{1-36}$ and the digests thereof can be determined by detecting $PYY_{1-36}$ and/or peptide digests that are generated by peptide compound $PYY_{1-36}$ degradation. Accordingly, the presence or absence of $PYY_{1-36}$ and the digests thereof, which may be present in the pharmaceutical formulation during production, can be easily and accurately (range of error within approximately 1 to 2%) determined by the determination method of the present invention.

Accordingly, the determination method of the invention is very effective means of qualitatively analyzing a $PYY_{3-36}$-containing pharmaceutical formulation.

BEST MODE FOR CARRYING OUT THE INVENTION

The present invention is described in further detail with reference to the following Reference Examples and Examples. However, the present invention is not limited thereto.

Reference Example 1

A 0.03 mmol/l Tyr-$NH_2$ solution (1.5 ml) was loaded into a reaction cell of an ultra-sensitive isothermal titration calorimeter VP-ITC (produced by MicroCal Inc.)

The colorimeter syringe was filled with a 0.3 mmol/l CB[7]-containing solution (0.25 ml).

Figure 2:
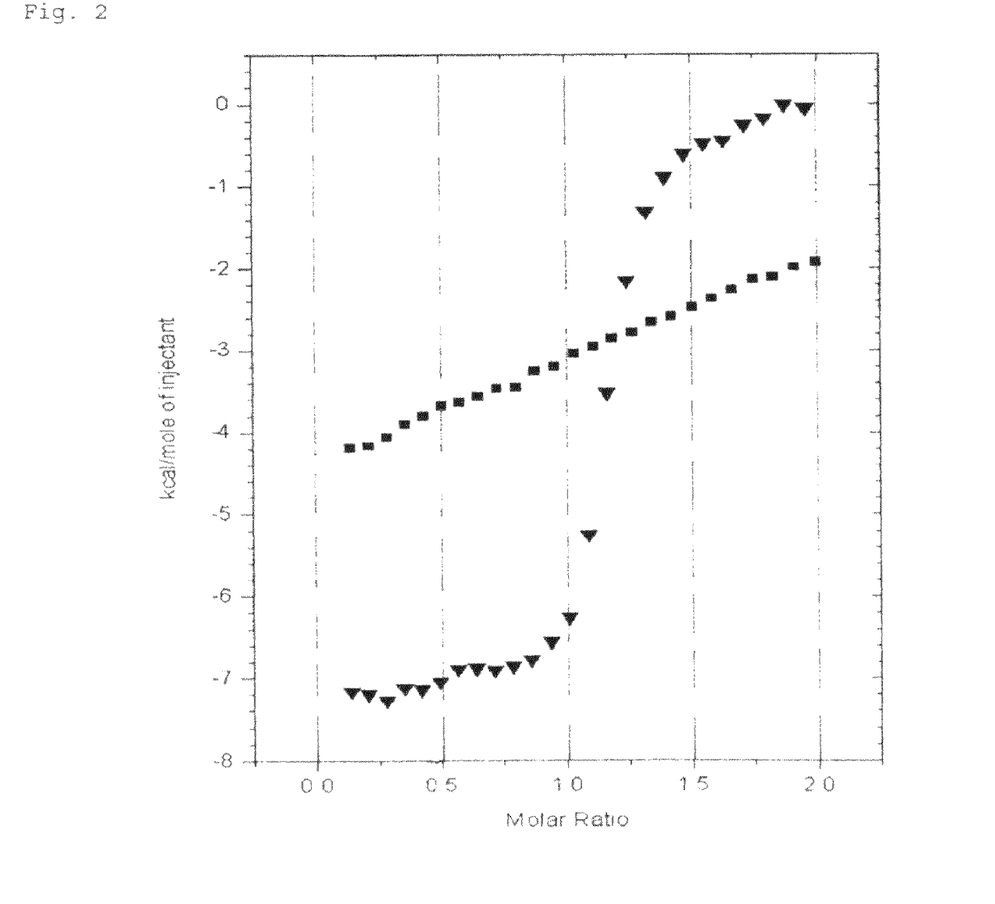
FIG. 2 is a graph in which the heat content (■) obtained in Reference Example 1 and the heat content (▼) obtained in the "Formation of Calibration Curve" in Example 1 are plotted.

The calorimeter was set in the state of thermal equilibrium, and 0.01 ml of CB[7]-containing solution was added to a reaction cell a total of 25 times. The resulting data was automatically integrated using ORIGIN 7.0 (produced by Micro-Cal Inc.) The results are shown in FIG. 2 (▼).

FIG. 1. reveals that the peptide compound having a tyrosine residue at the N-terminal is reacted with CB[7] (forming a complex) to generate heat.

Example 1

Formation of Calibration Curve

A solution (1.5 ml, concentration: 0.03 mmol/l) of $PYY_{3-36}$ represented by the following amino acid sequence: H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-$NH_2$ (SEQ ID NO: 16) was loaded into a reaction cell of an ultra-sensitive isothermal titration calorimeter VP-ITC (produced by MicroCal Inc.)

The colorimeter syringe was filled with a CB[7]-containing solution (0.25 ml, 0.3 mmol/l).

The calorimeter was set in the state of thermal equilibrium, and 0.01 ml of CB[7]-containing solution was added to a reaction cell 25 times in total. The resulting data was automatically integrated using ORIGIN 7.0 (produced by Micro-Cal Inc.) The results are shown in FIG. 2 (■).

Determination of the Presence or Absence of $PYY_{3-36}$

Subsequently, the pharmaceutical test formulation containing $PYY_{3-36}$ and Tyr-$NH_2$ (the molar ratio of $PYY_{3-36}$ to Tyr-$NH_2$ is 95:5) was dissolved in water to thereby prepare a 0.03 mmol/l pharmaceutical test formulation-containing solution. The resulting solution was loaded into a reaction cell of the calorimeter. Further, the colorimeter syringe was filled with 0.25 ml of CB[7]-containing solution.

Figure 3:
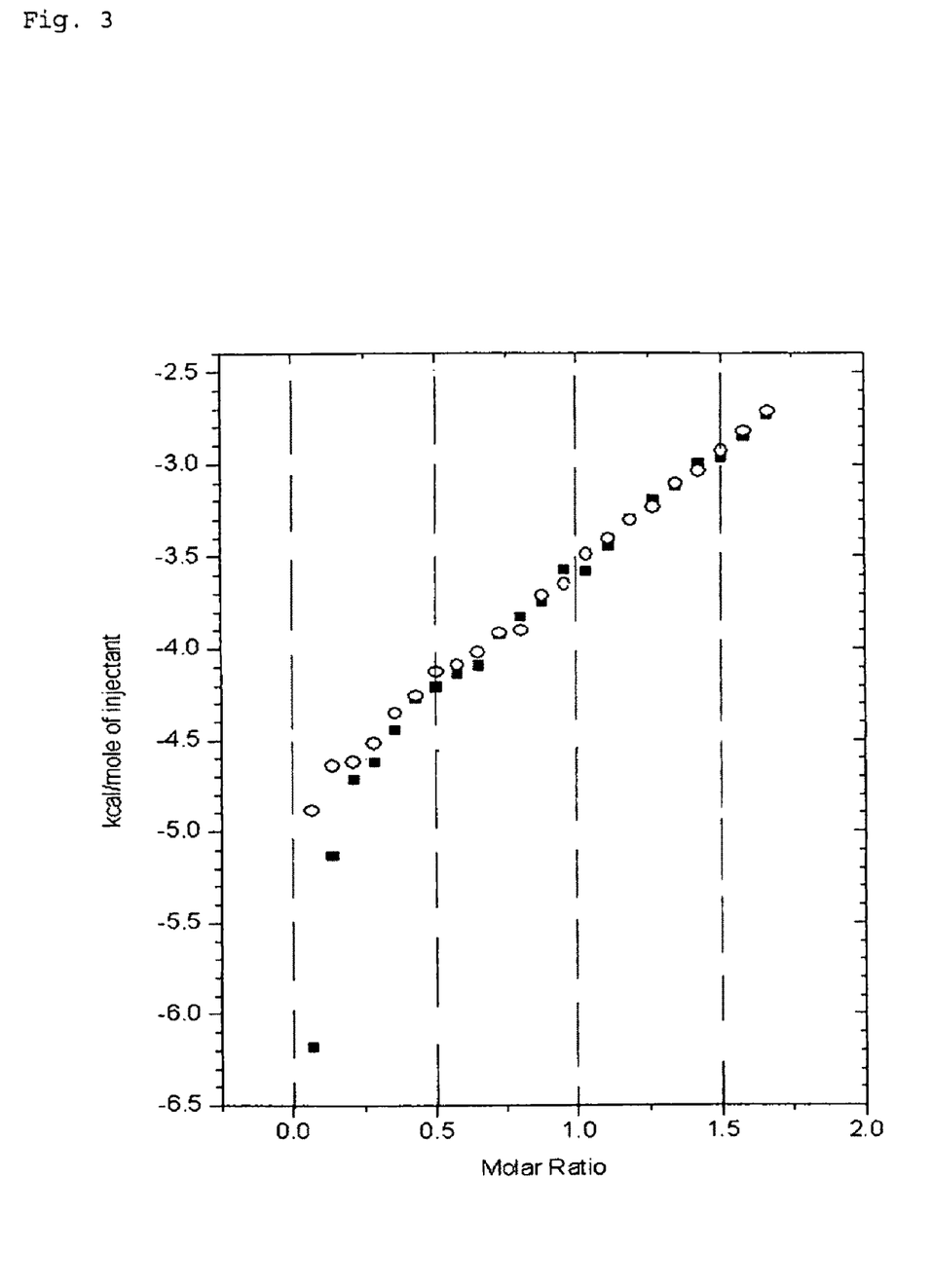
FIG. 3 is a graph in which the heat content (○) obtained in the "Formation of Calibration Curve" and the heat content (■) obtained in the "Determination of the Presence or Absence of $PYY_{3-36}$" in Example 1 are plotted.

The heat content was measured using the same method described above, and the resulting data was automatically integrated. The results (■) are shown in FIG. 3. The calibration curve (○) is also shown in FIG. 3 for comparison.

FIG. 3 reveals that the mixture of the pharmaceutical test formulation (the molar ratio of $PYY_{3-36}$ and Tyr-$NH_2$ is 95:5) generates more heat than that of pure $PYY_{3-36}$. Specifically, FIG. 3 reveals that, compared to pure $PYY_{3-36}$, the pharmaceutical test formulation includes Tyr-$NH_2$ to compensate for the shortage of $PYY_{3-36}$, which results in the difference in the heat quantity.

Example 2

Formation of Calibration Curve

Figure 4:
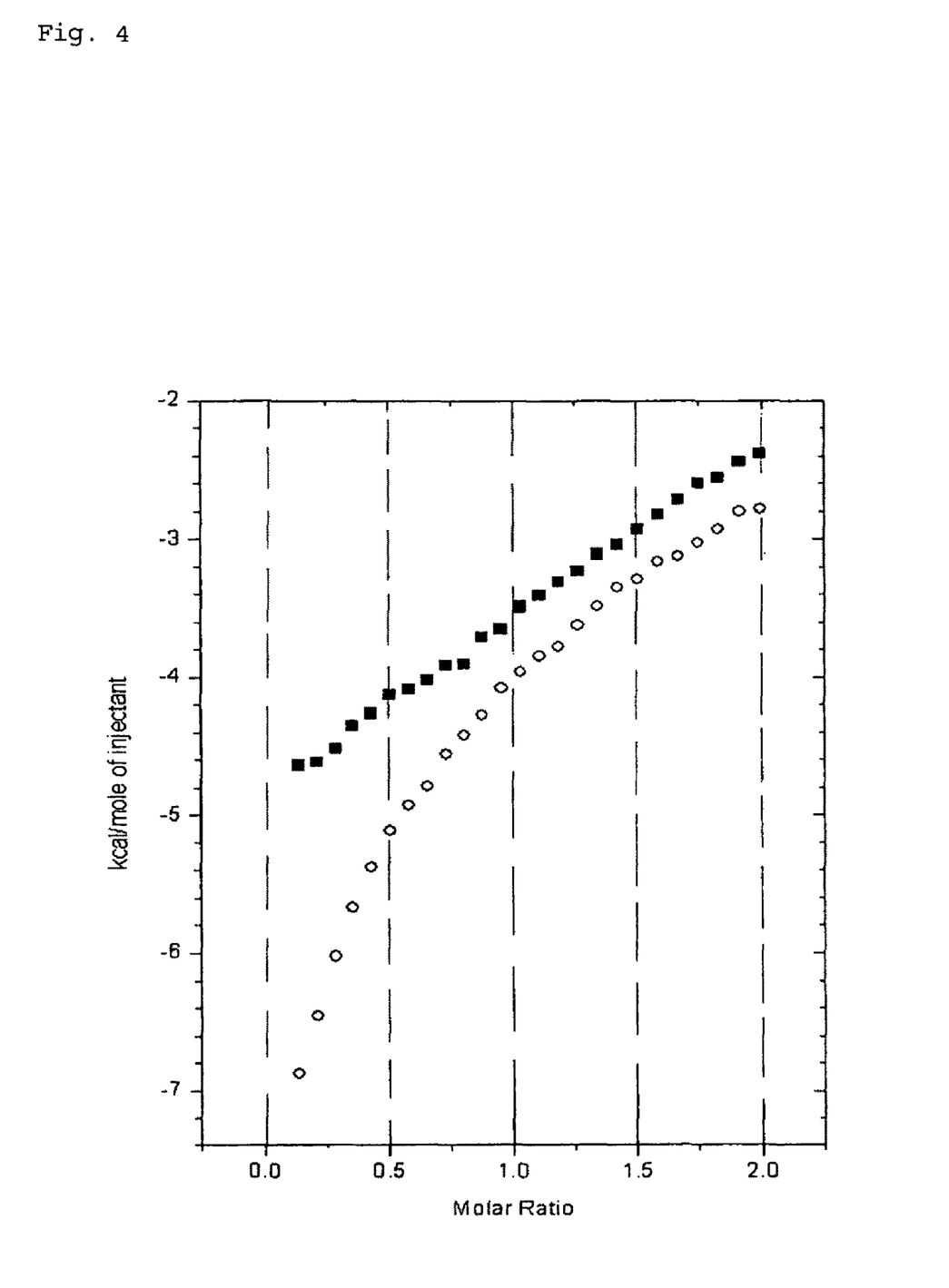
FIG. 4 is a graph in which the heat content (■) obtained in the "Formation of Calibration Curve" and the heat content (○) obtained in the "Determination of the Presence or Absence of $PYY_{3-36}$" in Example 2 are plotted.

A calibration curve was prepared in the same manner as in Example 1. The results (■) are shown in FIG. 4.
Determination of the Presence or Absence of $PYY_{3-36}$ ($PYY_{1-36}$)

Subsequently, the pharmaceutical test formulation containing $PYY_{3-36}$ and $PYY_{1-36}$ (the molar ratio of $PYY_{3-36}$ to $PYY_{1-36}$ is 95:5) was dissolved in water to thereby prepare a 0.03 mmol/l pharmaceutical test formulation-containing solution. The resulting solution was loaded into a reaction cell of the calorimeter. Further, the colorimeter syringe was filled with 0.25 ml of CB[7]-containing solution.

The heat content was measured using the same method described above, and the resulting data was automatically integrated. FIG. 4 shows the results (○).

FIG. 4 reveals that the mixture of the pharmaceutical test formulation (the molar ratio of $PYY_{3-36}$ and $PYY_{1-36}$ is 95:5) generates more heat than that of pure $PYY_{3-36}$. Specifically, FIG. 4 reveals that, compared to pure $PYY_{3-36}$, the pharmaceutical test formulation includes $PYY_{1-36}$ to compensate for the shortage of $PYY_{3-36}$, which results in the difference in the heat quantity.

The invention claimed is:

1. A method for determining in a pharmaceutical test formulation the presence or absence of a peptide compound $PYY_{3-36}$ represented by the following amino acid sequence: H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-X (SEQ ID NO: 1), wherein X is OH or a carboxy acid-protecting group, the method comprising:

(1) preparing a solution by mixing the pharmaceutical test formulation with cucurbit[7]uril in a solvent; and (2) thermally analyzing the solution prepared in Step (1) wherein generation of heat by the solution prepared in Step (1) evidences the existence of H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-X, wherein X is OH or a carboxy acid-protecting group.

2. The determination method according to claim 1, wherein the presence or absence of a peptide compound $PYY_{1-36}$ represented by the following amino acid sequence: H-Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-$NH_2$ (SEQ ID NO: 2), and/or peptide digests generated by degradation of the peptide compound $PYY_{1-36}$ is determined.

3. The determination method according to claim 1, wherein peptide digests generated by degradation of the peptide compound $PYY_{3-36}$ is detected.

* * * * *

SEQUENCE LISTING

```
<160> NUMBER OF SEQ ID NOS: 16

<210> SEQ ID NO 1
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ile having a hydrogen group
<220> FEATURE:
<221> NAME/KEY: MOD_RES
<222> LOCATION: (34)..(34)
<223> OTHER INFORMATION: Tyr having a hydroxyl group or a protecting
      group for carboxylic acid

<400> SEQUENCE: 1

Ile Lys Pro Glu Ala Pro Gly Glu Asp Ala Ser Pro Glu Glu Leu Asn
1               5                   10                  15
```

-continued

Arg Tyr Tyr Ala Ser Leu Arg His Tyr Leu Asn Leu Val Thr Arg Gln
            20                  25                  30

Arg Tyr

<210> SEQ ID NO 2
<211> LENGTH: 36
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Tyr having a hydrogen group
<220> FEATURE:
<221> NAME/KEY: MOD_RES
<222> LOCATION: (36)..(36)
<223> OTHER INFORMATION: Tyr having an amino group

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Tyr having a hydroxyl group or a protecting
      group for carboxylic acid

<400> SEQUENCE: 3

Tyr Leu Asn Leu Val Thr Arg Gln Arg Tyr
1               5                   10

<210> SEQ ID NO 4
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Tyr having a hydroxyl group or a protecting
      group for carboxylic acid

<400> SEQUENCE: 4

Tyr Tyr Ala Ser Leu Arg His Tyr Leu Asn Leu Val Thr Arg Gln Arg
1               5                   10                  15

Tyr

<210> SEQ ID NO 5
<211> LENGTH: 7
<212> TYPE: PRT
<213> ORGANISM: Homo sapiens

<400> SEQUENCE: 5

Tyr Tyr Ala Ser Leu Arg His
1               5

<210> SEQ ID NO 6
<211> LENGTH: 16
<212> TYPE: PRT

<213> ORGANISM: Homo sapiens

<400> SEQUENCE: 6

Tyr Tyr Ala Ser Leu Arg His Tyr Leu Asn Leu Val Thr Arg Gln Arg
1               5                   10                  15

<210> SEQ ID NO 7
<211> LENGTH: 9
<212> TYPE: PRT
<213> ORGANISM: Homo sapiens

<400> SEQUENCE: 7

Tyr Leu Asn Leu Val Thr Arg Gln Arg
1               5

<210> SEQ ID NO 8
<211> LENGTH: 33
<212> TYPE: PRT
<213> ORGANISM: Homo sapiens

<400> SEQUENCE: 8

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg

<210> SEQ ID NO 9
<211> LENGTH: 24
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ile having a hydrogen group

<400> SEQUENCE: 9

Ile Lys Pro Glu Ala Pro Gly Glu Asp Ala Ser Pro Glu Glu Leu Asn
1               5                   10                  15

Arg Tyr Tyr Ala Ser Leu Arg His
            20

<210> SEQ ID NO 10
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ile having a hydrogen group

<400> SEQUENCE: 10

Ile Lys Pro Glu Ala Pro Gly Glu Asp Ala Ser Pro Glu Glu Leu Asn
1               5                   10                  15

Arg

<210> SEQ ID NO 11
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Tyr having an amino group

<400> SEQUENCE: 11

```
Tyr Leu Asn Leu Val Thr Arg Gln Arg Tyr
1               5                   10

<210> SEQ ID NO 12
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Tyr having an amino group

<400> SEQUENCE: 12

Tyr Tyr Ala Ser Leu Arg His Tyr Leu Asn Leu Val Thr Arg Gln Arg
1               5                   10                  15

Tyr

<210> SEQ ID NO 13
<211> LENGTH: 35
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Tyr having a hydrogen group

<400> SEQUENCE: 13

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg
        35

<210> SEQ ID NO 14
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Tyr having a hydrogen group

<400> SEQUENCE: 14

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His
            20                  25

<210> SEQ ID NO 15
<211> LENGTH: 19
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Tyr having a hydrogen group

<400> SEQUENCE: 15

Tyr Pro Ile Lys Pro Glu Ala Pro Gly Glu Asp Ala Ser Pro Glu Glu
1               5                   10                  15

Leu Asn Arg

<210> SEQ ID NO 16
<211> LENGTH: 34
```

```
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ile having a hydrogen group
<220> FEATURE:
<221> NAME/KEY: MOD_RES
<222> LOCATION: (34)..(34)
<223> OTHER INFORMATION: Tyr having a hydroxyl group or a protecting
      group for carboxylic acid

<400> SEQUENCE: 16

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```